United States Patent
Hayashi et al.

(10) Patent No.: US 8,107,064 B2
(45) Date of Patent: Jan. 31, 2012

(54) DISC WAFER INSPECTING DEVICE AND INSPECTING METHOD

(75) Inventors: Yoshinori Hayashi, Yokohama (JP); Takeki Kogawa, Yokohama (JP); Hideki Mori, Yokohama (JP); Akimasa Hori, Yokohama (JP)

(73) Assignee: Shibaura Mechatronics Corporation, Yokohama-shi (JP)

( * ) Notice: Subject to any disclaimer, the term of this patent is extended or adjusted under 35 U.S.C. 154(b) by 539 days.

(21) Appl. No.: 12/376,469

(22) PCT Filed: Aug. 9, 2007

(86) PCT No.: PCT/JP2007/065597
§ 371 (c)(1), (2), (4) Date: Feb. 5, 2009

(87) PCT Pub. No.: WO2008/018537
PCT Pub. Date: Feb. 14, 2008

(65) Prior Publication Data
US 2010/0177953 A1    Jul. 15, 2010

(30) Foreign Application Priority Data

Aug. 10, 2006  (JP) .................................. 2006-218006
Mar. 30, 2007  (JP) .................................. 2007-091342

(51) Int. Cl.
*G01N 21/00* (2006.01)
(52) U.S. Cl. .................................................. 356/237.2
(58) Field of Classification Search .... 356/237.2–237.5, 356/625, 634, 635
See application file for complete search history.

(56) References Cited

U.S. PATENT DOCUMENTS

| 6,963,394 | B2* | 11/2005 | Yamamoto et al. | 356/237.4 |
| 7,737,426 | B2* | 6/2010 | Takahashi et al. | 250/559.36 |
| 7,800,748 | B2* | 9/2010 | Sakaguchi | 356/237.2 |
| 2006/0044571 | A1* | 3/2006 | Whitefield et al. | 356/625 |
| 2007/0064224 | A1* | 3/2007 | Kreh et al. | 356/237.2 |
| 2007/0139642 | A1* | 6/2007 | Ikeda et al. | 356/150 |
| 2007/0236689 | A1* | 10/2007 | Yoshida et al. | 356/237.2 |
| 2008/0225281 | A1* | 9/2008 | Komuro | 356/237.2 |

* cited by examiner

*Primary Examiner* — Layla Lauchman
(74) *Attorney, Agent, or Firm* — Kratz, Quintos & Hanson, LLP

(57) ABSTRACT

An inspecting device and an inspecting method enabling better precision inspection for a processing region formed on a surface of a semiconductor wafer or other disc wafer are provided. The inspecting device is configured having image capturing means 130a, 130b for capturing an image of an outer edge and its neighboring region of a rotating wafer 10, wafer outer edge position measuring means 200 for measuring the radial direction position of the outer edge at each of the plurality of rotational angle positions θn of the wafer 10 based on the images obtained by the image capturing means 130a, 130b, an edge-to-edge distance measuring means 200 for measuring the edge-to-edge distance $B_{\theta n}$ between the outer edge of the wafer 10 and the edge of an insulating film 11 at each of the plurality of rotational angle positions θn based on the images obtained by the image capturing means 130a, and an inspection information generating means 200 for generating predetermined inspection information based on the radial direction position $A_{\theta n}$ of the outer edge of the wafer 10 and the edge-to-edge distance $B_{\theta n}$.

18 Claims, 16 Drawing Sheets

【FIG.1】
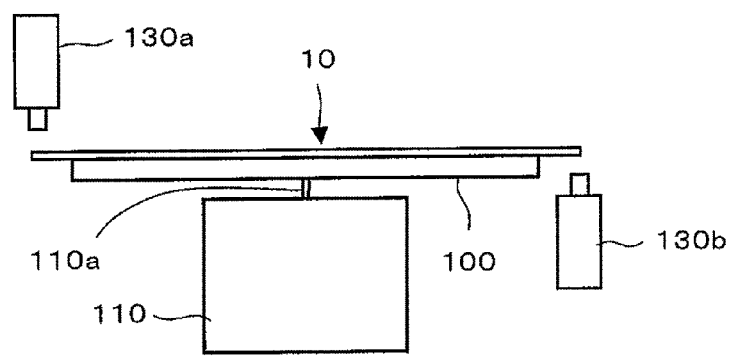
【FIG.2】
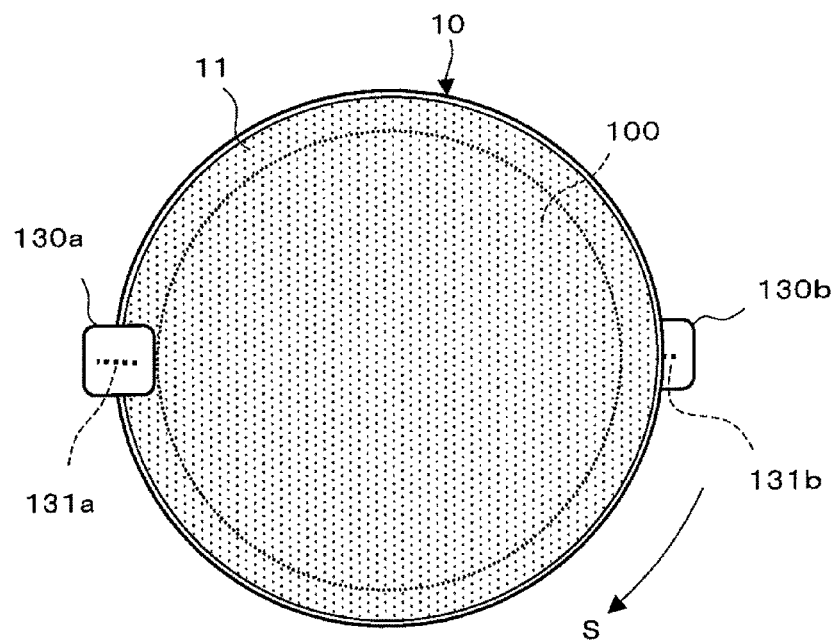

[FIG.3]
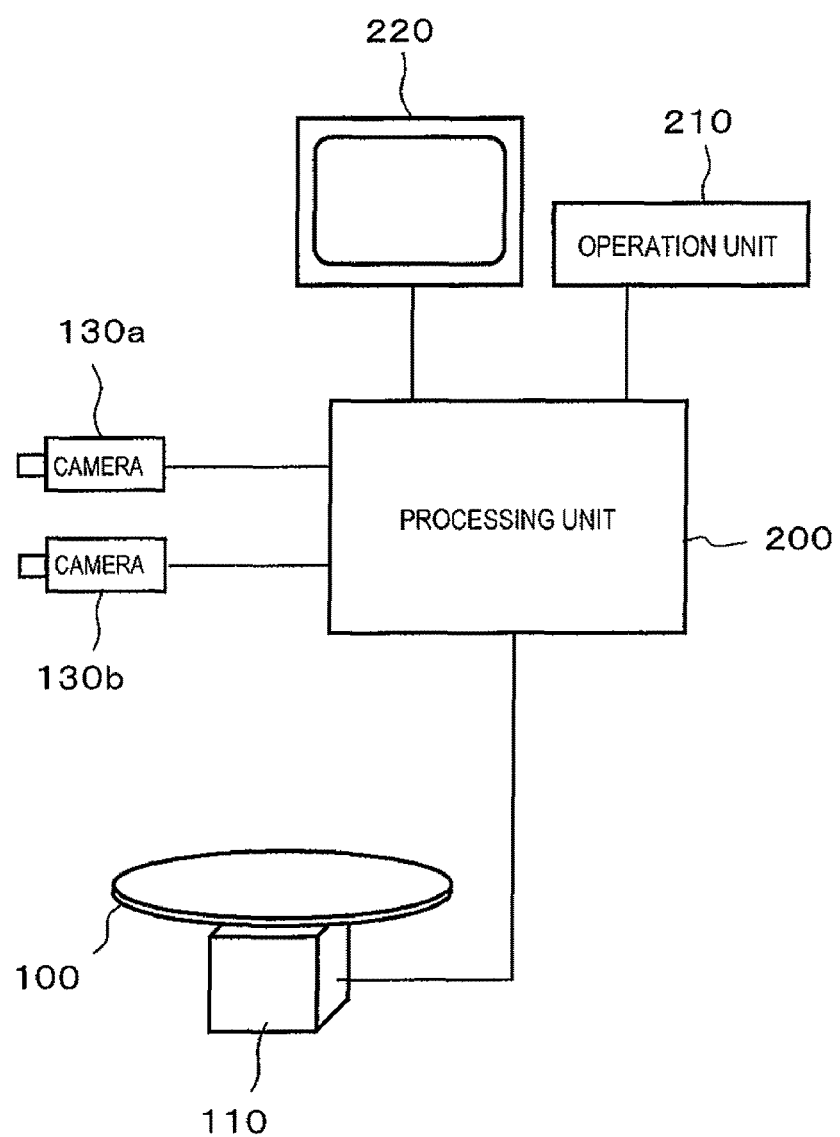

[FIG.4]
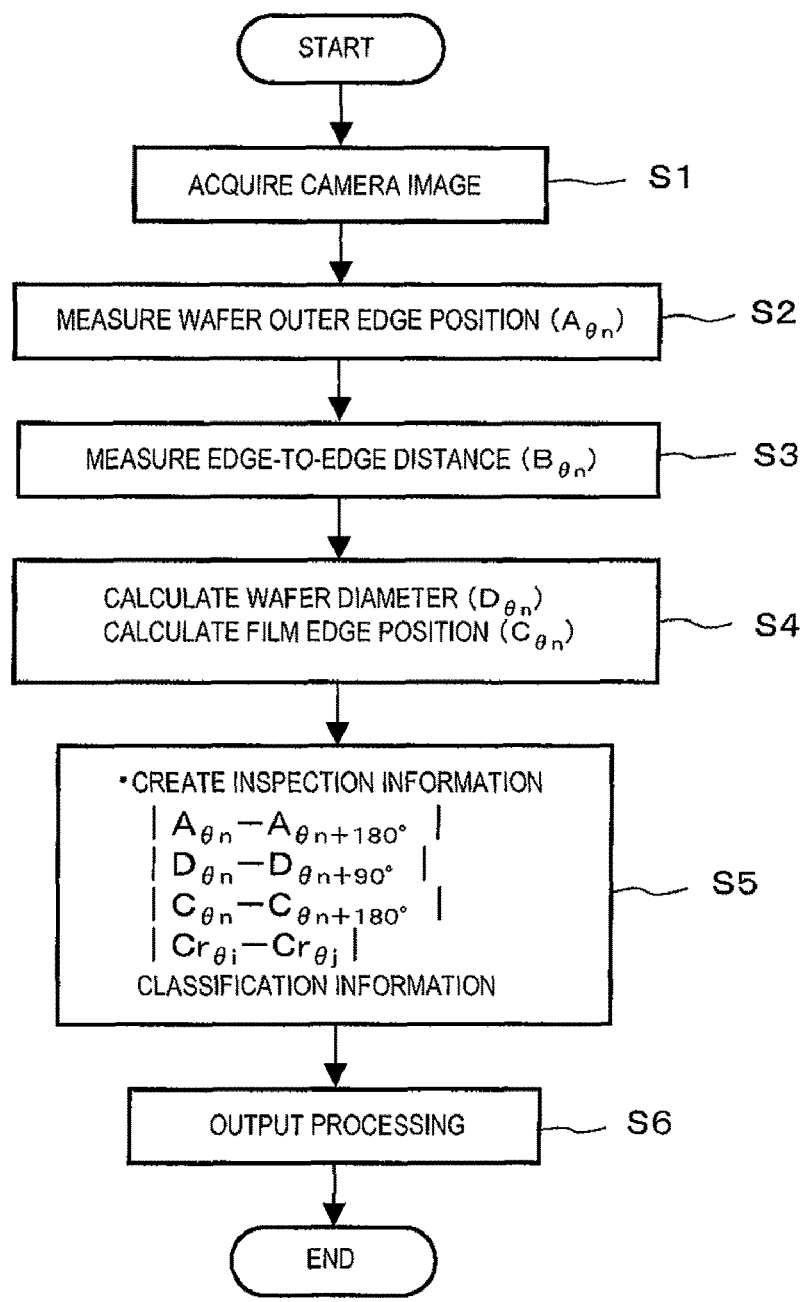

[FIG.5]
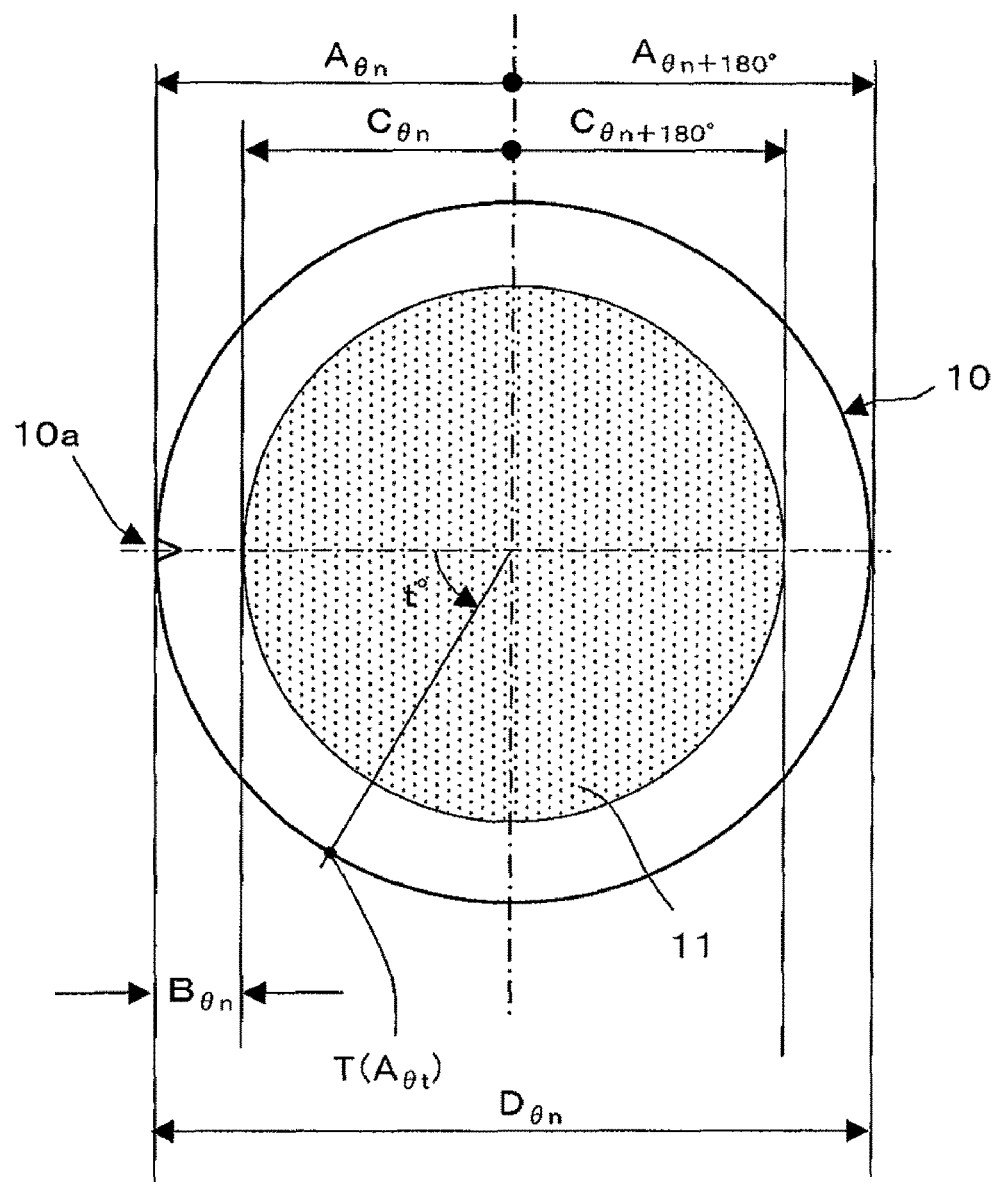

[FIG.6]
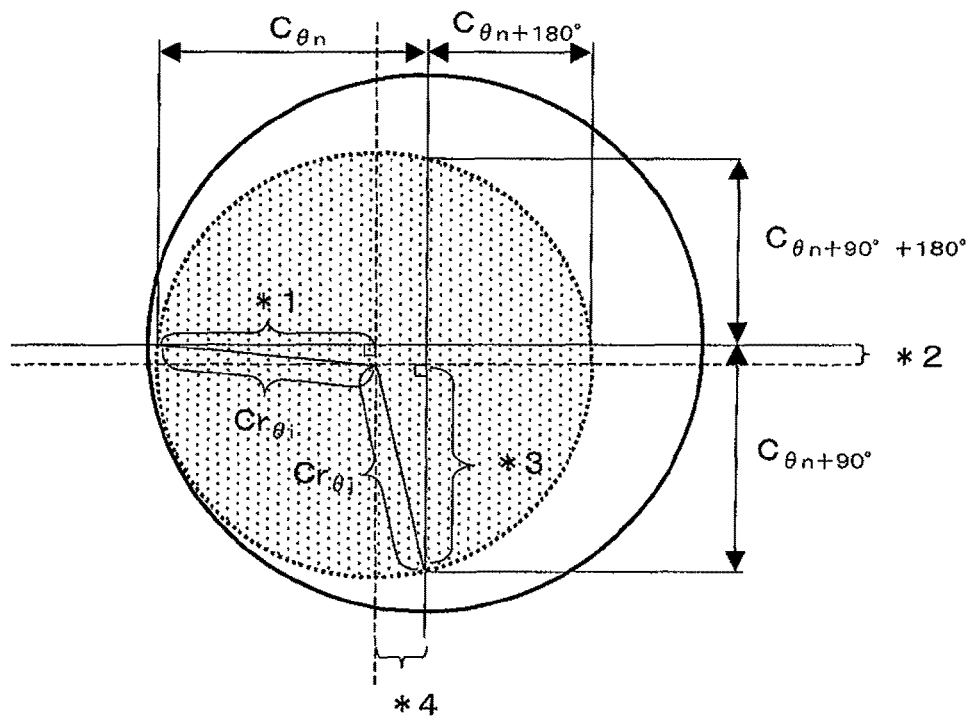
*1: $(C_{\theta n} + C_{\theta n+180°})/2$
*2: $|C_{\theta n+90°} - C_{\theta n+90°+180°}|/2$
*3: $(C_{\theta n+90°} + C_{\theta n+90°+180°})/2$
*4: $|C_{\theta n+180°} - C_{\theta n}|/2$
$$Cr_{\theta i} = (((C_{\theta n} + C_{\theta n+180°})/2)^2 + ((C_{\theta n+90°} - C_{\theta n+90°+180°})/2)^2)^{1/2}$$
$$Cr_{\theta j} = (((C_{\theta n+90°} + C_{\theta n+90°+180°})/2)^2 + ((C_{\theta n+180°} - C_{\theta n})/2)^2)^{1/2}$$

| NO.1 | EVALUATION |
|---|---|
| $\lvert D_{\theta n} - D_{\theta n+90°} \rvert < d$ | WAFER SHAPE : OK |
| $\lvert C_{\theta n} - C_{\theta n+180°} \rvert < c1$ | INSULATING FILM ECCENTRICITY : OK |
| $\lvert Cr_{\theta i} - Cr_{\theta j} \rvert < c2$ | INSULATING FILM SHAPE : OK |

(b)

| NO.2 | EVALUATION |
|---|---|
| $\lvert D_{\theta n} - D_{\theta n+90°} \rvert > d$ | WAFER SHAPE : NG |
| $\lvert C_{\theta n} - C_{\theta n+180°} \rvert < c1$ | INSULATING FILM ECCENTRICITY : OK |
| $\lvert Cr_{\theta i} - Cr_{\theta j} \rvert < c2$ | INSULATING FILM SHAPE : OK |

(c)

| NO.3 | EVALUATION |
|---|---|
| $\lvert D_{\theta n} - D_{\theta n+90°} \rvert > d$ | WAFER SHAPE : NG |
| $\lvert C_{\theta n} - C_{\theta n+180°} \rvert < c1$ | INSULATING FILM ECCENTRICITY : OK |
| $\lvert Cr_{\theta i} - Cr_{\theta j} \rvert > c2$ | INSULATING FILM SHAPE : NG |

(d)

| NO.4 | EVALUATION |
|---|---|
| $\lvert D_{\theta n} - D_{\theta n+90°} \rvert < d$ | WAFER SHAPE : OK |
| $\lvert C_{\theta n} - C_{\theta n+180°} \rvert < c1$ | INSULATING FILM ECCENTRICITY : OK |
| $\lvert Cr_{\theta i} - Cr_{\theta j} \rvert > c2$ | INSULATING FILM SHAPE : NG |

| NO.5 | EVALUATION |
|---|---|
| $\|D_{\theta n} - D_{\theta n+90°}\| < d$ | WAFER SHAPE : OK |
| $\|C_{\theta n} - C_{\theta n+180°}\| > c1$ | INSULATING FILM ECCENTRICITY : NG |
| $\|Cr_{\theta i} - Cr_{\theta j}\| < c2$ | INSULATING FILM SHAPE : OK |

(b)

| NO.6 | EVALUATION |
|---|---|
| $\|D_{\theta n} - D_{\theta n+90°}\| > d$ | WAFER SHAPE : NG |
| $\|C_{\theta n} - C_{\theta n+180°}\| > c1$ | INSULATING FILM ECCENTRICITY : NG |
| $\|Cr_{\theta i} - Cr_{\theta j}\| < c2$ | INSULATING FILM SHAPE : OK |

(c)

| NO.7 | EVALUATION |
|---|---|
| $\|D_{\theta n} - D_{\theta n+90°}\| > d$ | WAFER SHAPE : NG |
| $\|C_{\theta n} - C_{\theta n+180°}\| > c1$ | INSULATING FILM ECCENTRICITY : NG |
| $\|Cr_{\theta i} - Cr_{\theta j}\| > c2$ | INSULATING FILM SHAPE : NG |

(d)

| NO.8 | EVALUATION |
|---|---|
| $\|D_{\theta n} - D_{\theta n+90°}\| < d$ | WAFER SHAPE : OK |
| $\|C_{\theta n} - C_{\theta n+180°}\| > c1$ | INSULATING FILM ECCENTRICITY : NG |
| $\|Cr_{\theta i} - Cr_{\theta j}\| > c2$ | INSULATING FILM SHAPE : NG |

[FIG.9]
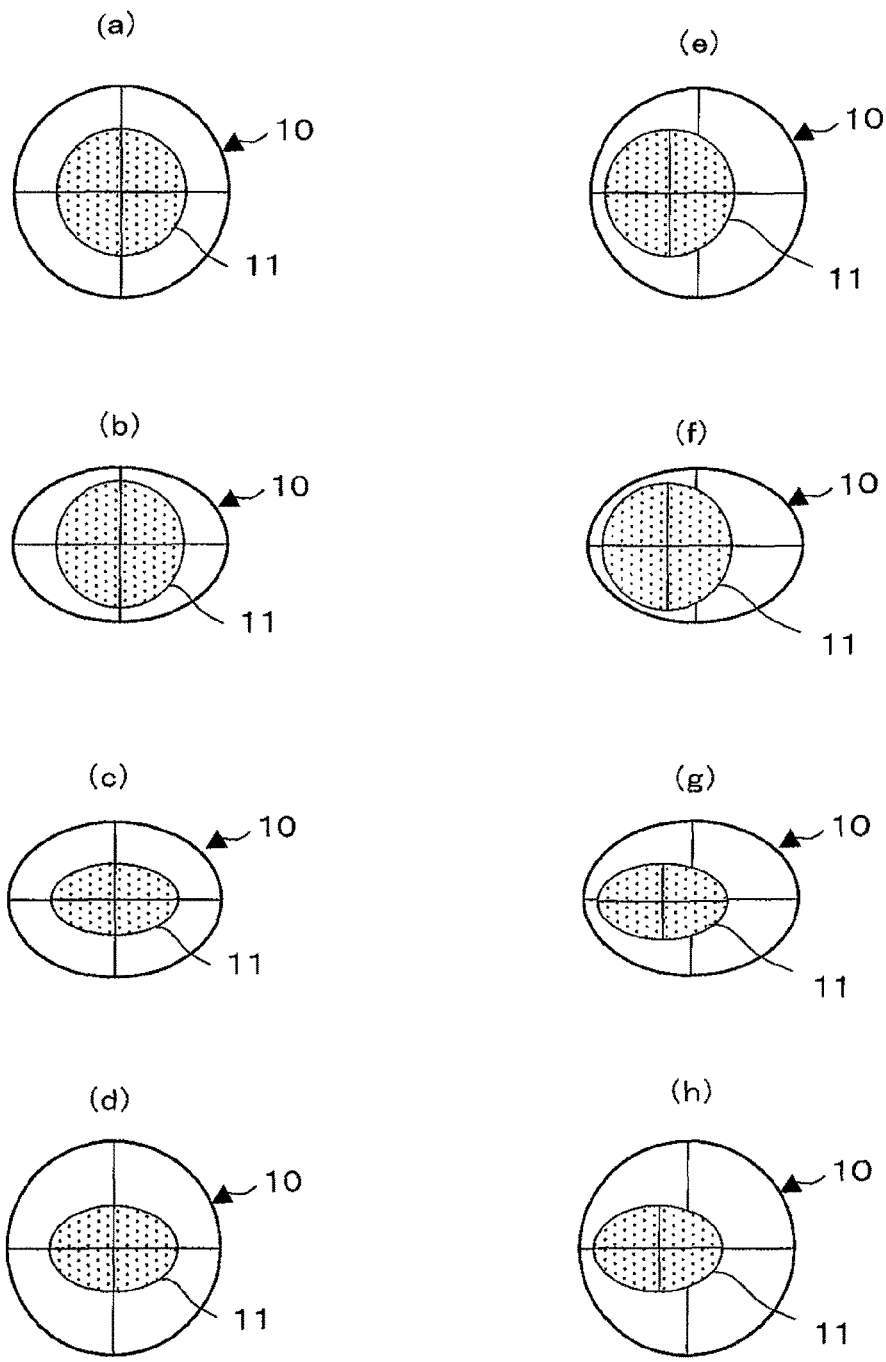

[FIG.10]
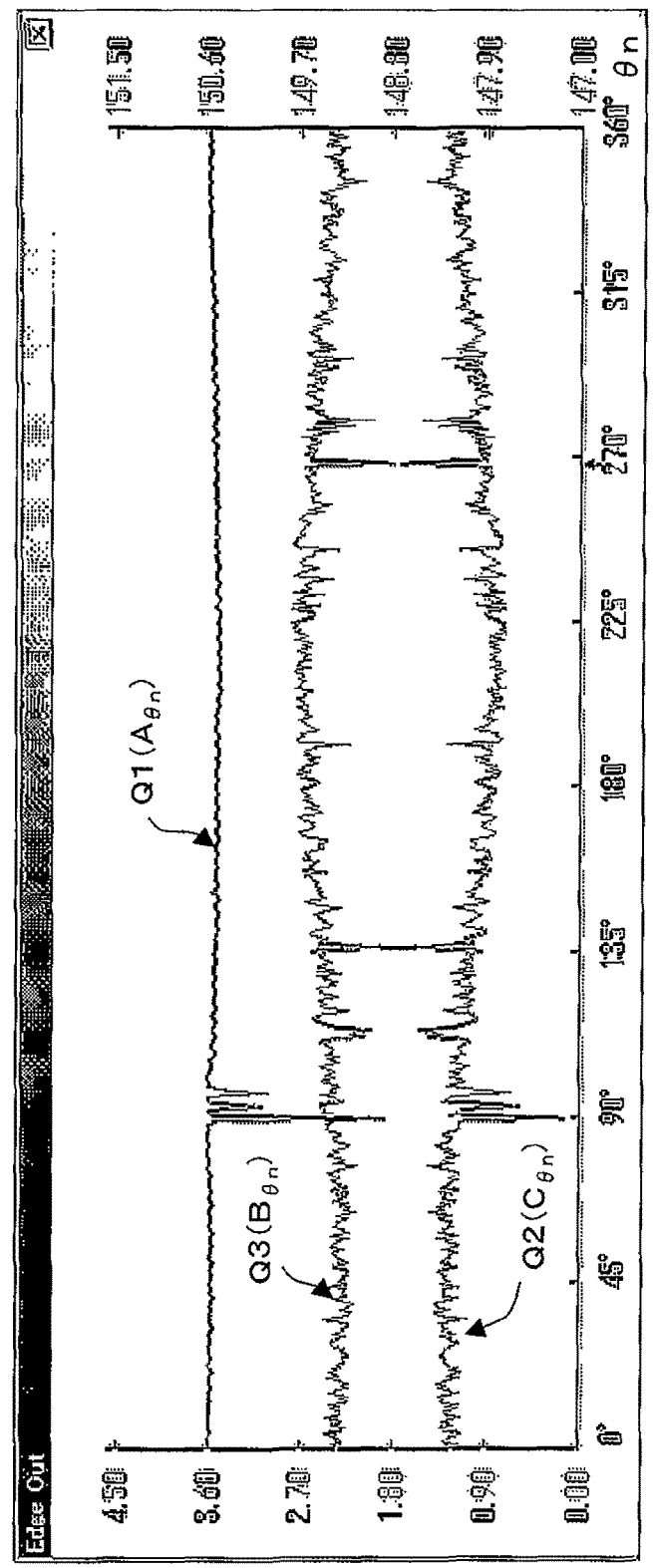

[FIG.11]
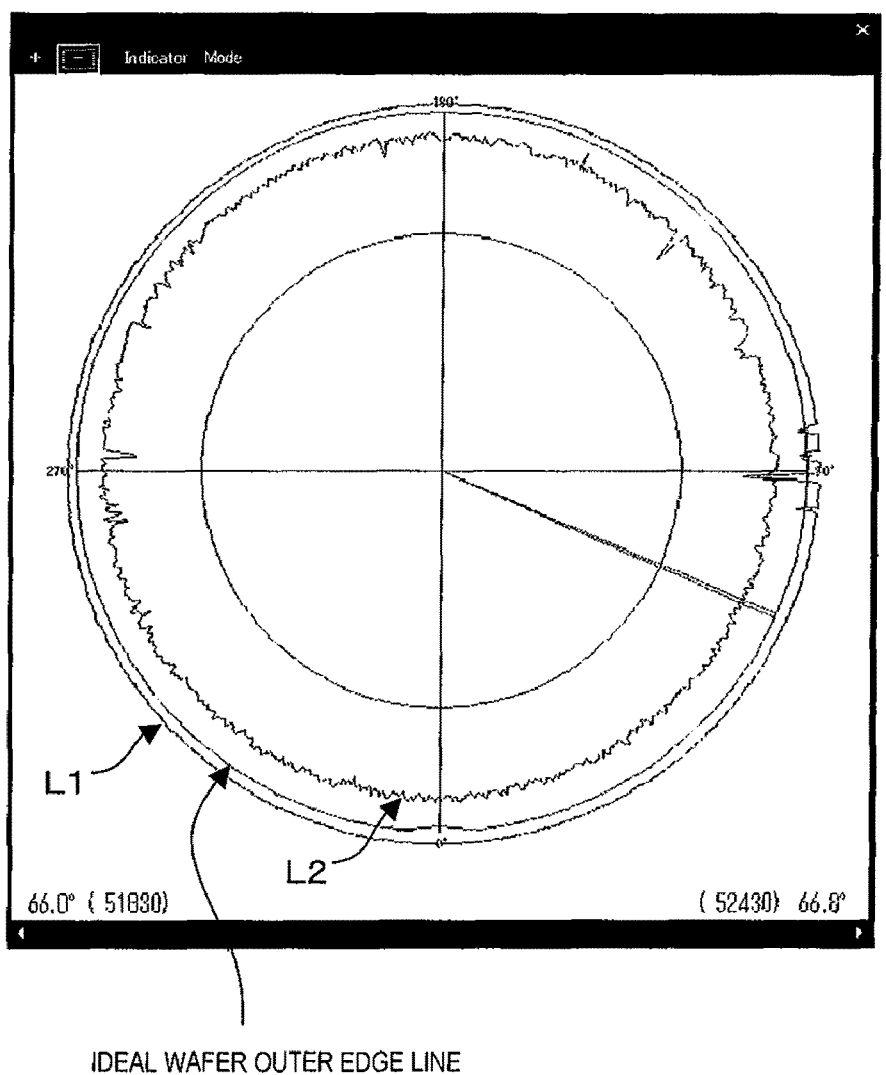
IDEAL WAFER OUTER EDGE LINE

[FIG.12]
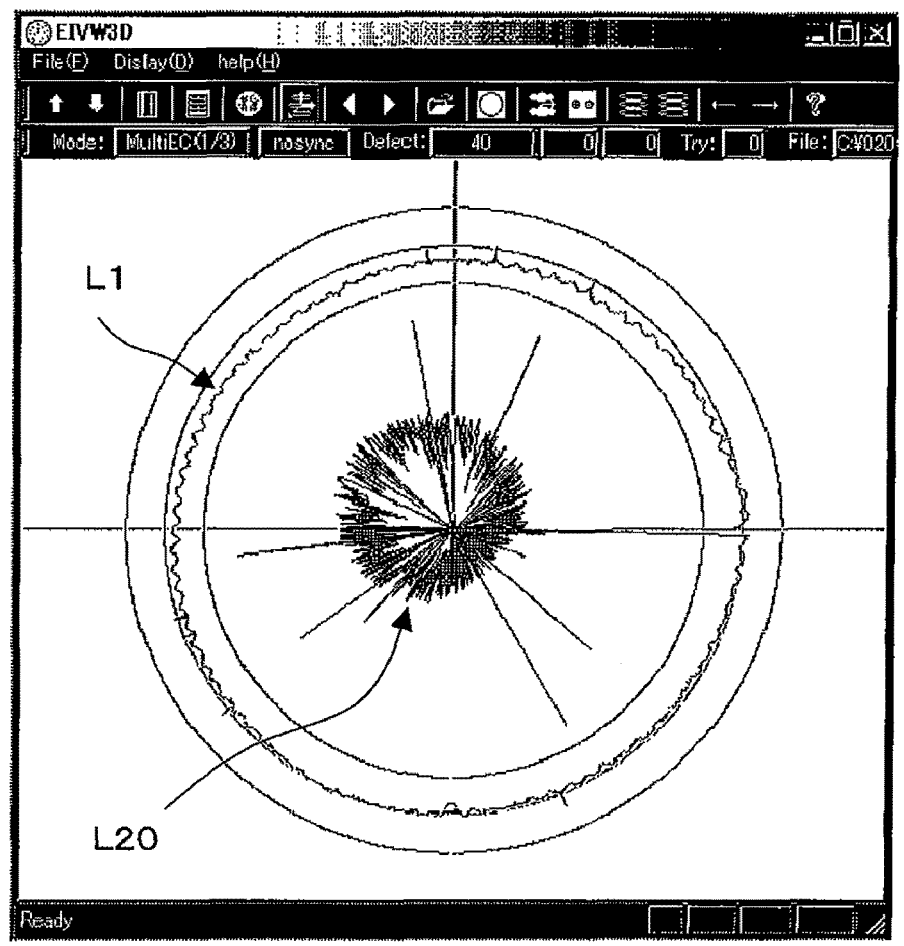

[FIG.13]
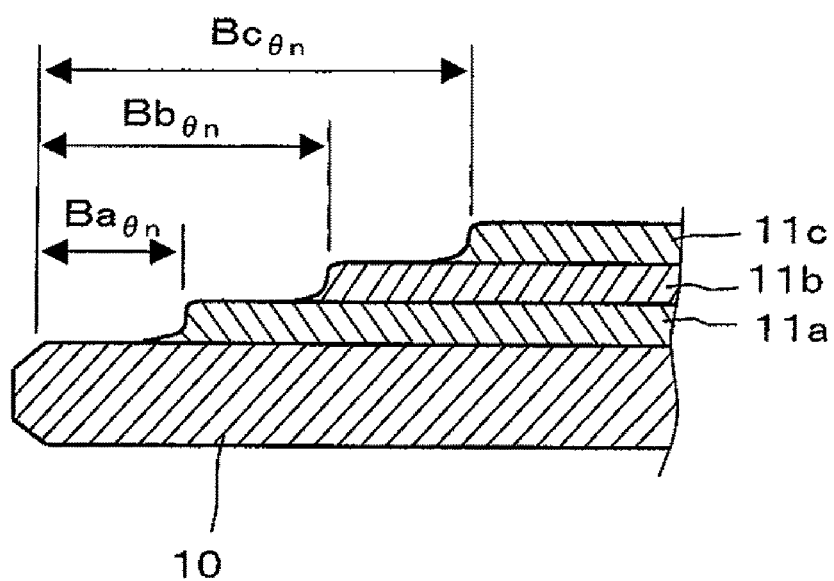

[FIG.14]
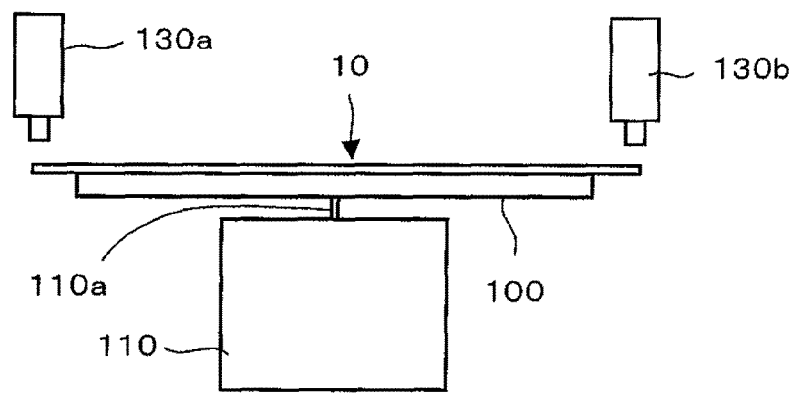
[FIG.15]
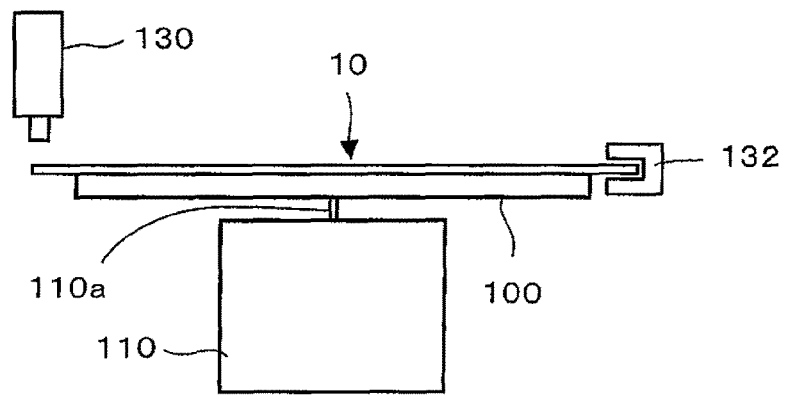

[FIG.16]
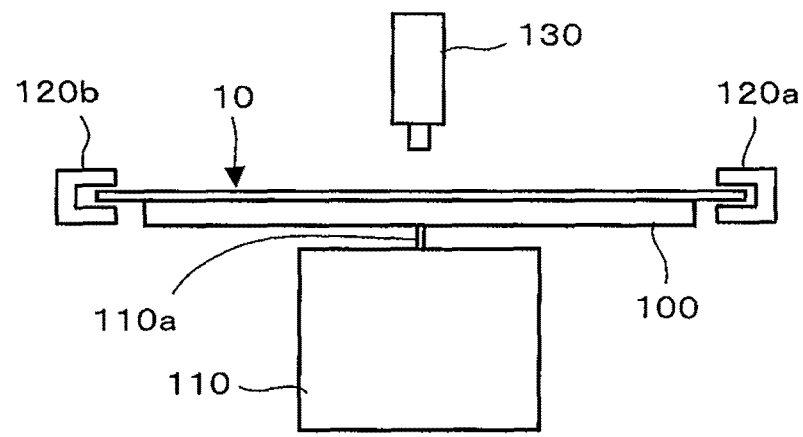
[FIG.17]
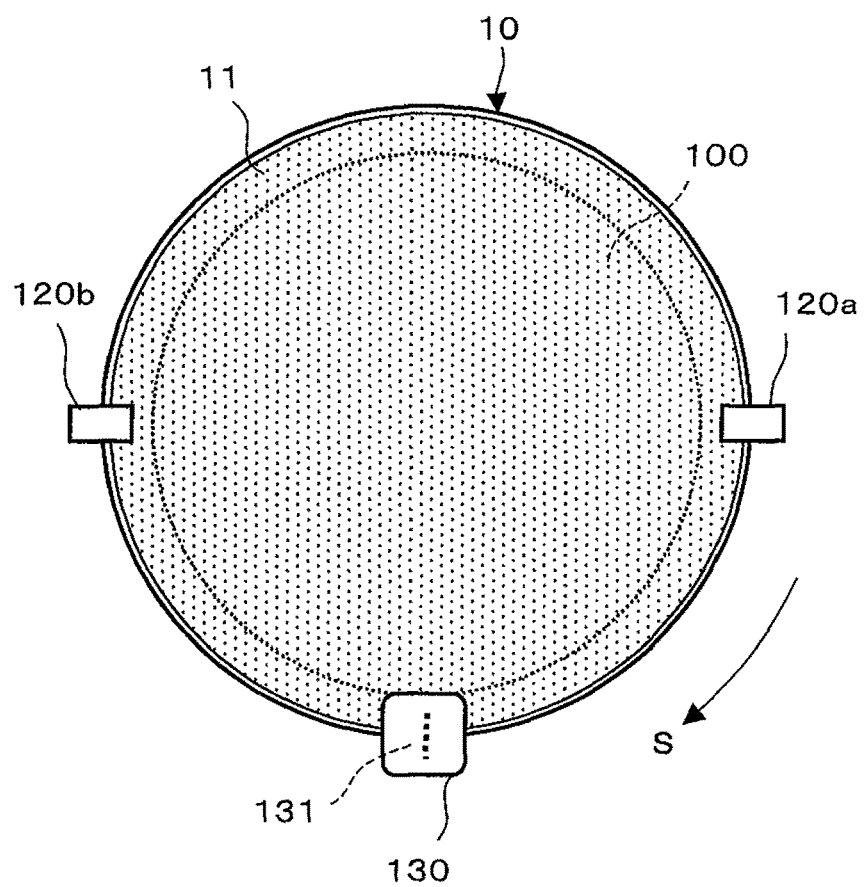

[FIG.18]
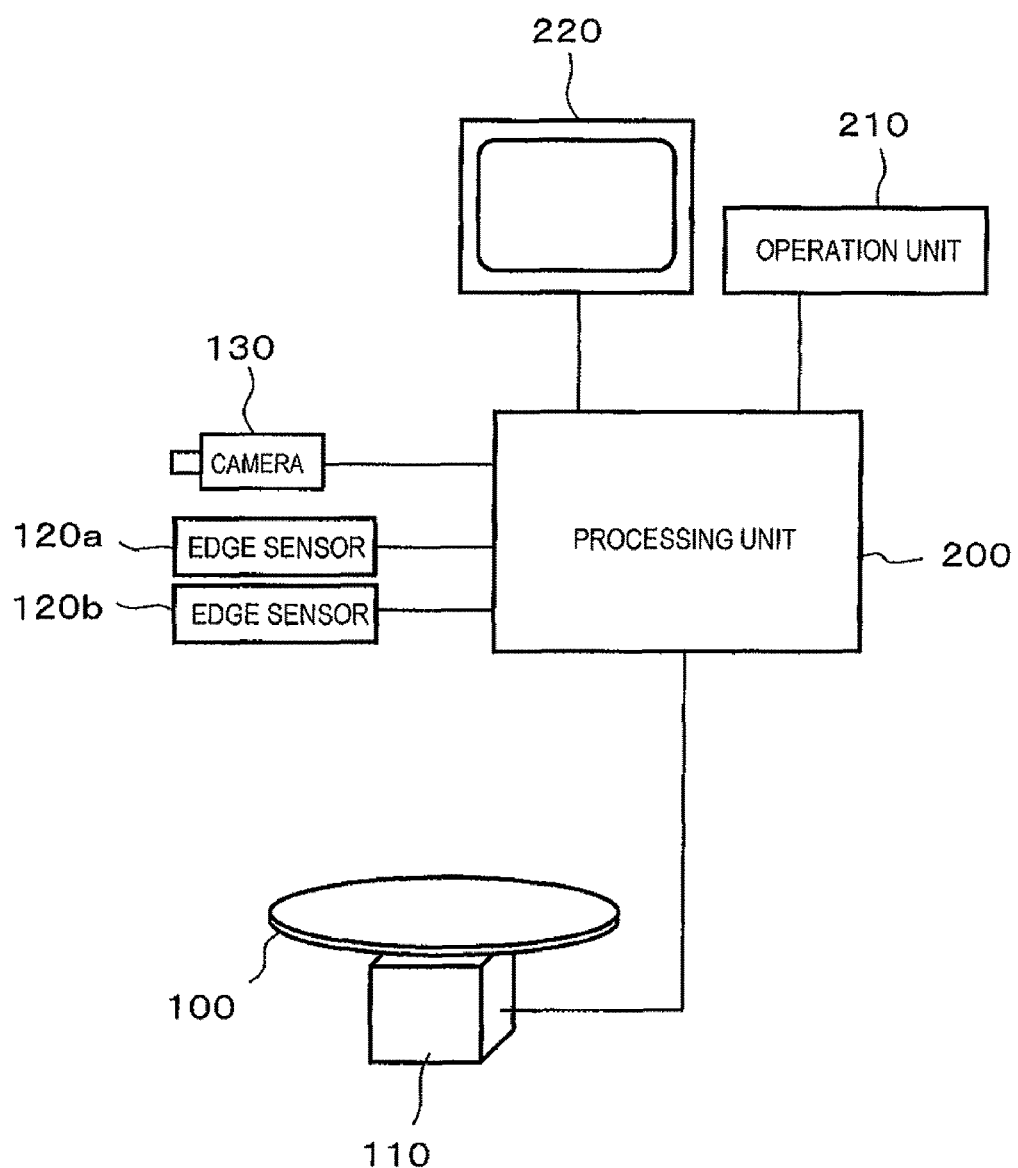

[FIG.19]
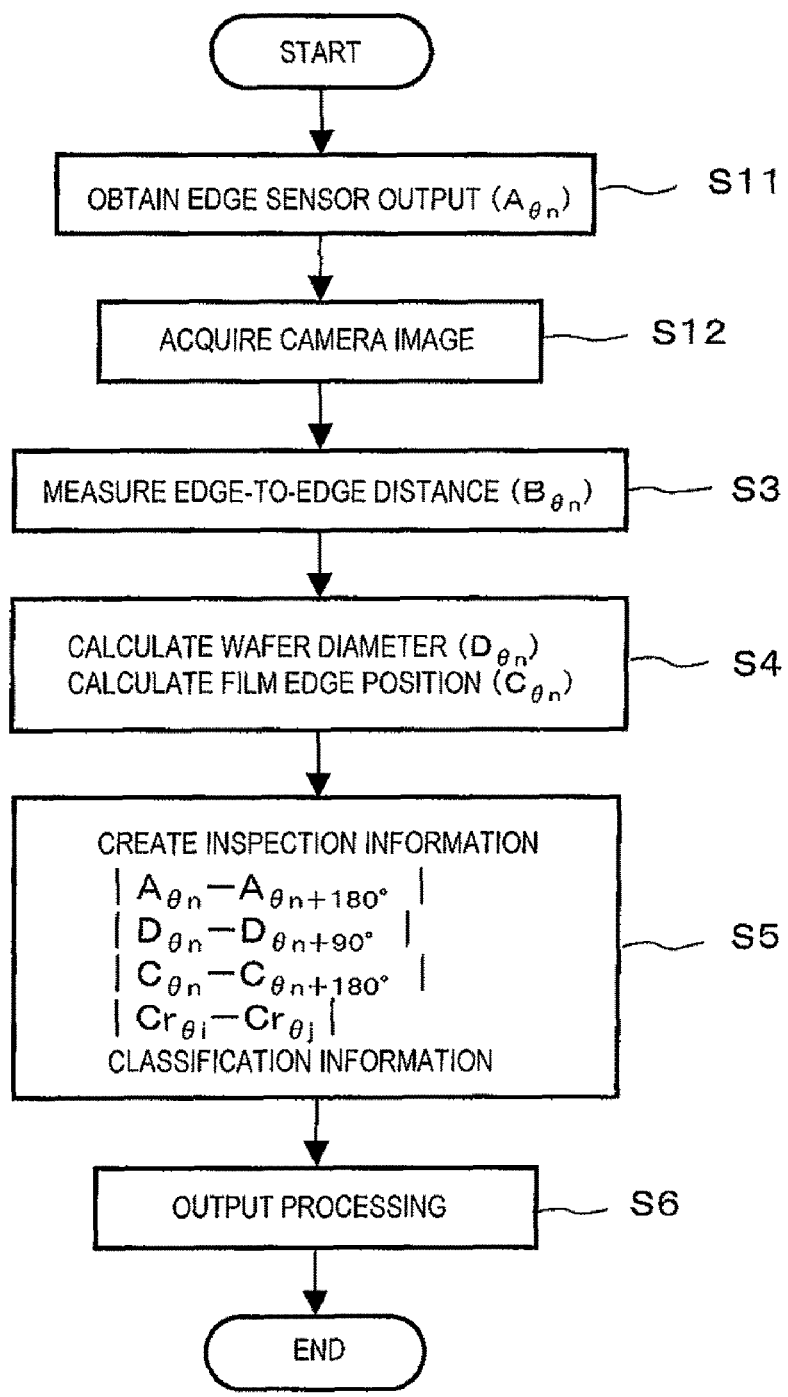

DISC WAFER INSPECTING DEVICE AND INSPECTING METHOD

TECHNICAL FIELD

The present invention relates to an inspecting device and inspecting method of a semiconductor wafer or other disc wafer, more particularly relates to an inspecting device and inspecting method for the inspection of a disc wafer on the surface of which an insulating film, conductive film, or other processing region is formed.

BACKGROUND ART

A semiconductor wafer (a type of disc wafer) is treated through a film forming process or etching process to for example concentrically form an insulating film, conductive film, or other processing region on the surface. In the past, the technique of determining whether the edge of the processing region (insulating film etc.) formed on this semiconductor wafer is in a properly finished state without curling etc. has been proposed (see Patent Document 1). This technique captures images of a plurality of locations of the outer edge of the semiconductor wafer and measures from the captured images the exposed width between the outer edge and the edge of the processing region at the plurality of locations of the semiconductor wafer so as to determine from the state of the exposed width at the plurality of locations whether the edge of the processing region (insulating film etc.) is in a proper finished state with no curling etc.
Patent Document 1: Japanese Patent Publication (A) No. 2002-134575

DISCLOSURE OF THE INVENTION

Problems to be Solved by the Invention

The conventional technique such as explained above inspects and evaluates the finished state of the edge of the processing region based on the state of exposed width between the outer edge of the semiconductor wafer (disc wafer) and the edge of the processing region formed on the surface. That is, it evaluates the shape of the processing region by the exposed width under the assumption that the shape of the outer edge of the semiconductor wafer is always normal (for example, a perfect circle). However, the shape of the outer edge of the semiconductor wafer affecting the exposed width is not necessarily constant and may fluctuate when seen in detail. Therefore, the conventional technique cannot evaluate the processing region formed on the surface of a disc wafer with a good precision.

The present invention was made for the purpose of solving such conventional problems and provides an inspecting device and inspecting method able to inspect a processing region formed on the surface of a semiconductor wafer or other disc wafer with a better precision.

Means for Solving the Problems

The disc wafer inspecting device according to the present invention is configured as an inspecting device of a disc wafer having a processing region formed on its surface having a holder rotatable about a predetermined shaft and holding the disc wafer, a rotation drive part making the holder rotate about the shaft, an image capturing means for capturing an image of the outer edge and its neighboring region of the disc wafer rotated by the rotation of the holder, a wafer outer edge position measuring means for measuring a radial direction position of the outer edge of said disc wafer at each of a plurality of rotational angle positions of the disc wafer rotated by rotation of the holder, an edge-to-edge distance measuring means for measuring an edge-to-edge distance between an outer edge of the disc wafer and an edge of the processing region at each of the plurality of rotational angle positions based on the images captured by the image capturing means, and an inspection information generating means for generating predetermined inspection information based on the radial direction position of the outer edge at each of the plurality of rotational angle positions of the disc wafer obtained by the wafer outer edge position measuring means and the edge-to-edge distance at each of the plurality of rotational angle positions obtained by the edge-to-edge distance measuring means.

Due to this configuration, the radial direction position of the outer edge at each of the plurality of rotational angle positions of the disc wafer becomes information showing the shape of the outer edge of the disc wafer, so the inspection information generated based on the radial direction position of the outer edge at each of the plurality of rotational angle positions of the disc wafer and the edge-to-edge distance between the outer edge of the disc wafer and the processing region formed on the surface of said disc wafer at each of the plurality of rotational angle positions can become information enabling evaluation of the shape of the processing region formed on the surface of the disc wafer considering the shape of the outer edge of the disc wafer.

Further, the disc wafer inspecting device according to the present invention can be configured so that the inspection information generating means has a processing region edge position calculating means for calculating radial direction positions of the edge at the plurality of rotational angle positions of the processing region based on the radial direction position of the outer edge at each of the plurality of rotational angle positions of the disc wafer and the edge-to-edge distance at the corresponding rotational angle position and generates inspection information based on the radial direction position of the edge at each of the plurality of rotational angle positions of the processing region.

Due to this configuration, inspection information based on the radial direction position of the outer edge at each of the plurality of rotational angle positions of the processing region formed on the surface of the disc wafer is generated, so it is possible to use said inspection information to evaluate the state of actual shape of the edge of the processing region and the relative position with respect to the disc wafer.

Further, the disc wafer inspecting device according to the present invention can be configured so that the inspection information includes information showing inspection results relating to a degree of eccentricity of the processing region to the disc wafer.

Due to this configuration, it is possible to inspect the degree of eccentricity to the disc wafer of the processing region formed on the surface of the disc wafer Further, the disc wafer inspecting device according to the present invention can be configured so that the inspection information includes information showing inspection results relating to a degree of circularity of the processing region.

Due to this configuration, it is possible to inspect the degree of circularity of the processing region formed on the surface of a disc wafer.

Further, the disc wafer inspecting device according to the present invention can be configured so that the inspection information generating means comprises a diameter calculating means for calculating a diameter at each of the plurality of rotational angle positions of said disc wafer based on a radial direction position of the outer edge at each of the plurality of rotational angle positions of the disc wafer and generates inspection information based on the diameter at each of the plurality of rotational angle positions of the disc wafer.

Due to this configuration, inspection information based on the diameter of a disc wafer formed with a processing region on its surface at each of the plurality of rotational angle positions is generated, so it is possible to evaluate the state of the shape of the outer edge of the disc wafer itself in based on said inspection information.

Further, the disc wafer inspecting device according to the present invention can be configured so that the inspection information includes information showing inspection results relating to a degree of eccentricity of the disc wafer to the shaft of the holder.

Due to this configuration, it is possible to inspect whether the degree of eccentricity of the disc wafer to the shaft of the holder holding the disc wafer, that is, the holding state of the disc wafer by the holder is appropriate or not.

Further, the disc wafer inspecting device according to the present invention can be configured so that the inspection information includes information showing inspection results relating to a degree of circularity of the disc wafer.

Due to this configuration, it is possible to inspect the degree of circularity of the disc wafer itself.

Further, the disc wafer inspecting device according to the present invention can be configured so that the inspection information generating means has a processing region edge position calculating means for calculating radial direction positions of the edge at the plurality of rotational angle positions of the processing region based on the radial direction position of the outer edge at each of the plurality of rotational angle positions of the disc wafer and the edge-to-edge distance at the corresponding rotational angle position and a diameter calculating means for calculating a diameter at each of a plurality of rotational angle position of the disc wafer based on the radial direction position of the outer edge at each of the plurality of rotational angle positions of the disc wafer and generates inspection information based on the radial direction position of the edge at each of the plurality of rotational angle positions of the processing region and the diameter at each of the plurality of rotational angle positions of the disc wafer.

Due to this configuration, inspection information based on the radial direction position of the edge at each of the plurality of rotational angle positions of the processing region formed on the surface of a disc wafer and the diameter at each of the plurality of rotational angle positions of said disc wafer is generated, so it is possible to use that inspection information to evaluate the state of the shape of the outer edge of the disc wafer and the state of the shape of the edge of the processing region formed on the surface of the disc wafer.

Further, the disc wafer inspecting device according to the present invention can be configured so that the inspection information includes classification information relating to the disc wafer and processing region generated based on the radial direction position of the edge at each of the plurality of rotational angle positions of the processing region and the diameter at each of the plurality of rotational angle positions of the disc wafer.

Due to this configuration, classification information relating to the disc wafer and processing region is generated as inspection information based on the radial direction position of the edge of the processing region at each of the plurality of rotational angle positions and the diameter of the disc wafer, so it is possible to evaluate the disc wafer and the processing region by that classification.

Further, the disc wafer inspecting device according to the present invention can be configured so that the wafer outer edge position measuring means measures the radial direction position of the outer edge of said disc wafer at each of the plurality of the rotational angle positions of the disc wafer based on the images captured by the image capturing means.

Due to this configuration, the images obtained by capturing the image of the outer edge and its neighboring region of the disc wafer are used for measuring the edge-to-edge distance and also are utilized for measuring the radial direction position of the outer edge of said disc wafer at each of the plurality of angular positions of the disk wafer, so the hardware configuration can be obtained more simply.

Further, the disc wafer inspecting device according to the present invention can be configured so that the image capturing means has a plurality of camera units set so as to be arranged around the disc wafer held by the holder and capturing images of the outer edge and its neighboring region of the disc wafer.

Due to this configuration, images are obtained from the plurality of camera units arranged around the disc wafer rotating along with the rotation of the holder, so even without making the disc wafer rotate once, the radial direction position of the outer edge of said disc wafer at each of the plurality of rotational angle positions across the entire circumference of the disc wafer can be measured. Further, if making the disc wafer rotate once, one circumference's worth of images of the disc wafer are obtained from each of the plurality of camera units, so a plurality of radial direction positions can be obtained for each of the plurality of rotational angle positions. Accordingly, a single radial direction position is determined from the plurality of radial direction positions obtained for each of the plurality of rotational angle positions (for example, a mean value), so a radial direction position with higher precision can be obtained.

Further, the disc wafer inspecting device according to the present invention can be configured so that the plurality of camera units have a first camera unit capturing an image of the outer edge and its neighboring region of the disc wafer held by the holder from one surface side and a second camera unit capturing an image of the outer edge and its neighboring region of the disc wafer from the other surface side.

Due to this configuration, images can be obtained for both surfaces of the disc wafer, so the radial direction position of the outer edge of the disc wafer at each of the plurality of rotational angle positions can be measured based on both images and the edge-to-edge distance at each of the plurality of rotational angle positions can be measured based on the images captured from the camera unit capturing images of the surface on which the processing region is formed. Further, images of the surface on which no processing region is formed can also be obtained, so it is also possible to create inspection information based on those images.

Further, the disc wafer inspecting device according to the present invention can be configured so that the first camera unit and the second camera unit are arranged offset from each other by a rotational angle of 180 degrees of the disc wafer.

Due to this configuration, it is possible to calculate the diameter able to show the shape of the outside of the disc wafer from the radial direction position of the disc wafer at each of the plurality of rotational angle positions measured based on the images obtained by the first camera unit and second camera unit at the same timing.

Further, the disc wafer inspecting device according to the present invention can be configured so that the wafer outer edge position measuring means measures the radial direction position of the outer edge of the disc wafer at each of the plurality of rotational angle positions based on both an image captured by the first camera unit and an image captured by the second camera unit.

Further, the disc wafer inspecting device according to the present invention can be configured the edge-to-edge distance measuring means measures the edge-to-edge distance based on the image obtained by the one of the camera units, among the first camera unit and second camera unit, capturing an image from the surface side where the process region is formed.

The disc wafer inspecting method according to the present invention is an inspecting method of the disc wafer having a processing region on its surface having an image capturing step of capturing an image of an outer edge and its neighboring region of a disc wafer held by a holder rotating about a predetermined shaft and rotating together with said holder, a wafer outer edge position measuring step of measuring a radial direction position of the outer edge of said disc wafer at each of a plurality of rotational angle positions of the disc wafer rotating by the rotation of the holder, an edge-to-edge distance measuring step of measuring an edge-to-edge distance between the outer edge of the disc wafer and the processing region at each of the plurality of rotational angle positions based on the images captured at the image capturing step, and an inspection information generating step of generating predetermined inspection information based on the radial direction position of the outer edge at each of the plurality of rotational angle positions of the disc wafer obtained by the wafer outer edge position measuring step and the edge-to-edge distance at each of the plurality of rotational angle positions obtained at the edge-to-edge distance measuring step.

Further, the disc wafer inspecting method according to the present invention can be configured so that the inspection information generating step includes a processing region edge position calculating step of calculating the radial direction position of the edge at each of the plurality of rotational angle positions of the processing region based on the radial direction position of the outer edge at each of the plurality of rotational angle positions of the disc wafer and the edge-to-edge distance at the corresponding rotational angle position and a diameter calculating step of calculating the diameter at each of the plurality of rotational angle positions of the disc wafer based on the radial direction position of the outer edge at each of the plurality of rotational angle positions of the disc wafer and generates inspection information based on the radial direction position of the edge at each of the plurality of rotational angle positions of the processing region and the diameter at each of the plurality of rotational angle positions of the disc wafer.

Further, the disc wafer inspecting method according to the present invention can be configured so that the wafer outer edge position measuring step measures the radial direction position of the outer edge of said disc wafer at each of the plurality of rotational angle positions of the disc wafer based on the images captured by the image capturing step.

Effects of the Invention

According to the inspecting device and inspecting method of a disc wafer according to the present invention, the generated inspection information can become information enabling evaluation of the shape of the processing region formed on the surface of the disc wafer considering the shape of the outer edge of the disc wafer, so it becomes possible to inspect the processing region formed on the surface of the disc wafer with a better precision.

BRIEF DESCRIPTION OF THE DRAWINGS

[FIG. 1] is a view showing the configuration of a mechanical system of an inspecting device of a semiconductor wafer (disc wafer) according to an embodiment of the present invention (first example of configuration).

[FIG. 2] is a view showing the state of the inspecting device shown in FIG. 1 when seen from above.

[FIG. 3] is a block diagram showing the configuration of a processing system of an inspecting device of a semiconductor wafer according to an embodiment of the present invention.

[FIG. 4] is a flow chart showing the processing routine at a processing unit in the processing system shown in FIG. 3.

[FIG. 5] is a view showing the parameters defined for a semiconductor wafer and an insulating film (processing region) formed on its surface.

[FIG. 6] is a view showing the parameters defined for an insulating film formed on the surface of a semiconductor wafer.

[FIG. 7] is a view showing classifications of wafers (part 1).

[FIG. 8] is a view showing classifications of wafers (part 2)

[FIG. 9] is a view schematically showing the states of the wafers and the insulating films in the different classifications.

[FIG. 10] is a view showing profiles of the wafer edge position $A_{\theta n}$, the film edge position $C_{\theta n}$, and the edge-to-edge distance $B_{\theta n}$ with respect to the rotational angle positions θn shown at the display unit.

[FIG. 11] is a view showing an example of an outer edge line of a wafer and an edge line of an insulating film shown at the display unit.

[FIG. 12] is a view showing another example of an outer edge line of a wafer and an edge line of an insulating film shown at the display unit.

[FIG. 13] is a view showing a cross-sectional structure of a semiconductor wafer on the surface of which a plurality of insulating films are laminated and an edge-to-edge distance for each insulating film.

[FIG. 14] is a view showing a second example of the configuration of a mechanical system of an inspecting device of a semiconductor wafer.

[FIG. 15] is a view showing a third example of the configuration of a mechanical system of an inspecting device of a semiconductor wafer.

[FIG. 16] is a view showing a fourth example of the configuration of a mechanical system of an inspecting device of a semiconductor wafer.

[FIG. 17] is a view showing the state of an inspecting device shown in FIG. 16 when seen from above.

[FIG. 18] is a block diagram showing the configuration of a processing system of an inspecting device having the mechanical system shown in FIG. 16 and FIG. 17.

[FIG. 19] is a flow chart showing a processing routine of a processing unit in the processing system shown in FIG. 15.

DESCRIPTION OF NOTATIONS 10 wafer (disc wafer)
11 insulating film (processing region)
100 stage (holder)
110 rotation drive motor (rotation drive part)
120a, 120b edge sensors
130a first camera unit 130b second camera unit
131, 131a, 131b CCD line sensors
132 edge sensor
200 processing unit
210 operation unit
220 display unit

BEST MODE FOR CARRYING OUT THE INVENTION

Below, embodiments of the present invention will be explained based on the drawings.

A mechanical system of an inspecting device of a semiconductor wafer (disc wafer) according to an embodiment of the present invention (first example of configuration) is configured as shown in FIG. 1 and FIG. 2. FIG. 1 is a view showing the mechanical system of the inspecting device seen from the side, and FIG. 2 is a view showing the mechanical system of said inspecting device seen from above.

In FIG. 1 and FIG. 2, a stage 100 (holder) is held on a shaft 110a of a rotation drive motor 110 (rotation drive part) and is continuously rotated in one direction (in the present embodiment, the clockwise direction shown as an arrow S). A semiconductor wafer constituting a disc wafer (below, simply referred to as a "wafer") 10 is set on the stage 100 in a horizontal state. Note that, at the stage 100, an alignment mechanism (not shown) is provided. Said wafer 10 is set on the stage 100 so that the center of the wafer 10 matches the center of rotation of the stage 100 (axial center of the shaft 110a) as much as possible.

On the surface of the wafer 10, for example an insulating film 11 (shaded area in FIG. 2: processing region view) is formed. A first camera unit 130a for capturing an image of the outer edge and its neighboring region of the wafer 10 set at the stage 100 from the front surface side of said wafer 10 is provided at a predetermined position above the stage 100, while a second camera 130b for capturing an image of the outer edge and its neighboring region of the wafer 10 from the back surface side of said wafer 10 is provided at a predetermined position below the stage 100. The pair of the first camera unit 130a and the second camera unit 130b are arranged offset by a rotational angle of 180 degrees of the wafer 10 set on the stage 100, that is, so as to be aligned in the direction of the diametrical line of the wafer 10. The first camera unit 130a and the second camera unit 130b include the CCD line sensors 131a, 131b and are set so that the line-shaped image capturing regions of the CCD line sensors 131a and 131b cross the outer edge of the wafer 10 on the stage 100 and the edge of the insulating film 11 and are toward the center of rotation of the stage 100.

The processing system of the evaluation system having the mechanical system of the above-mentioned configuration is configured as shown in FIG. 3.

In FIG. 3, imaging signals from the first camera unit 130a and the second camera unit 130b are input into a processing unit 200. This processing unit 200 performs the drive control of the rotation drive motor 110 so as to make the stage 100 rotate at a predetermined speed and processes the imaging signals from the first camera unit 130a and second camera unit 130b in accordance with an operation signal from an operation unit 210 as described later. Further, the processing unit 200 can display information obtained in the process of the processing at the display unit 220.

Next, the processing at the inspecting device will be explained.

Before a wafer 10 is actually processed, first, said inspecting device is initialized. In this initialization, for example a dummy wafer confirmed to be a perfect circle and to be accurate in size (for example, diameter 300 mm) is set on the stage 100 using an alignment mechanism (not shown) so that its center accurately matches the center of rotation of said stage 100. The processing unit 200 acquires image data (brightness data or density data of pixel units) based on the imaging signals from the first camera unit 130a and second camera unit 130b in the state when making the stage 100 rotate. Further, the parameters are initialized at the processing unit 200 so that the pixel positions corresponding to the outer edge (edge) of the dummy wafer at each rotational angle position θn at predetermined intervals are detected from the acquired images (image data) captured from the first camera unit 130a and from the acquired images (image data) captured from the second camera unit 130b and so that said pixel positions at each rotational angle position θn are recognized as radial direction positions from the center corresponding to the radius of the dummy wafer (for example, 150 mm).

Note that, in the present embodiment, this initialization is performed only once before usage of the inspecting device and performed each time the size of a wafer 10 being inspected is changed. However, it may be performed for each inspection of a wafer 10 or for each inspection of a preset number of wafers 10.

After finishing the initialization, in place of the dummy wafer, a wafer 10 being inspected is set on said stage 100 by an alignment mechanism (not shown) so that its center matches the center of rotation of the stage 100 as much as possible. Further, when a predetermined operation is performed at the operation unit 210, the processing unit 200 performs processing according to the routine shown in FIG. 4.

In FIG. 4, the processing unit 200 receives as input the imaging signals from the first camera unit 130a and the second camera unit 130b while the wafer 10 is rotating once at a constant speed to acquire the corresponding captured images (image data) (S1). Further, the processing unit 200 performs so-called edge extraction processing and thereby stores the pixel positions corresponding to the outer edge of the wafer 10 at each rotational angle position θn at each predetermined angular interval at each acquired image linked with each rotational angle position θn as a radial direction position $A_{\theta n}$ of the outer edge of the wafer 10 shown in FIG. 5 (below, referred to as "wafer edge position") (S2: wafer outer edge position measuring step).

Here, the rotational angle positions θn will be explained. As shown in FIG. 5, a wafer 10 is formed with a notch 10a at its outer circumference. Therefore, in the present embodiment, the position at this wafer 10 where the notch 10a is formed is set as the position of the rotational angle of 0 degree (=$\theta_0$). Accordingly, in the wafer 10 shown in FIG. 5, the rotational angle position of the position separated from the rotational angle position ($\theta_0$) in a counterclockwise direction by for example t degrees is defined as $\theta_t$, and the wafer edge position T of this rotational angle position is expressed as $A_{\theta t}$.

In this regard, when two wafer edge positions $A_{\theta n}$ are obtained for each rotational angle position θn based on the two images corresponding to the imaging signals from the first camera unit 130a and the second camera unit 130b obtained while the wafer 10 rotates once, their mean value can be stored as the true wafer edge position $A_{\theta n}$ corresponding to the rotational angle position θn. Further, it is also possible to obtain the wafer edge position $A_{\theta n}$ corresponding to each rotational angle position θn for half of the circumference of the wafer 10 from the images captured by the first camera unit 130a and the wafer edge position $A_{\theta n}$ corresponding to each rotational angle position θn for the remaining half of the circumference of the wafer 10 from the images captured by the second camera unit 130b.

Next, the processing unit 200 measures the edge-to-edge distance $B_{\theta n}$ between the outer edge of the wafer 10 and the edge of the insulating film 11 at each rotational angle position θn on the image expressed by the image data based on the imaging signal from the first camera unit 130a capturing images of the outer edge and its neighboring region from the surface side of the wafer 10 where the insulating film 11 is formed (S3: edge-to-edge distance measuring step). Specifically, the number of pixels between the outer edge of the wafer 10 and the edge of the insulating film 11 on the image loaded in the memory, for example, is measured and that number of pixels is converted to distance (edge-to-edge distance).

By doing so, if the wafer edge position $A_{\theta n}$ and the edge-to-edge distance $B_{\theta n}$ between the outer edge of the wafer 10 and the edge of the insulating film 11 are obtained for one circumference of the wafer 10, the processing unit 200 calculates the diameter $D_{\theta n}$ of the wafer 10 and the radial direction position of the edge $C_{\theta n}$ of the insulating film 11 (below, referred to as the "film edge position") at each rotational angle position θn (S4). Specifically, the sum of the wafer edge position $A_{\theta n}$ stored linked with each rotational angle position θn and the wafer edge position $A_{\theta n+180°}$ stored linked with the rotational angle position θn+180° rotated 180 degrees from the rotational angle position is calculated as the diameter $D_{\theta n}$ (see FIG. 5).

$$D_{\theta n} = A_{\theta n} + A_{\theta n+180°}$$

Further, the processing unit 200 subtracts from the wafer edge position $A_{\theta n}$ stored linked with each rotational angle position θn the edge-to-edge distance $B_{\theta n}$ at the corresponding rotational angle position θn so as to calculate the film edge position $C_{\theta n}$ (see FIG. 5).

$$C_{\theta n} = A_{\theta n} - B_{\theta n}$$

Afterwards, the processing unit 200 generates inspection information (evaluation information) of the wafer 10 based on the wafer edge position $A_{\theta n}$, diameter $D_{\theta n}$, and film edge position $C_{\theta n}$ at each rotational angle position θn obtained as explained above (S5: inspection information generating step). It is also possible to generation inspection information as follows.

The absolute value of the difference between the wafer edge position $A_{\theta n}$ at each rotational angle position θn and the wafer edge position $A_{\theta n+180}$ at the rotational angle position $\theta_{n+180}$ rotated 180° from that rotational angle position θn $$|A_{\theta n} - A_{\theta n+180°}|$$

can be generated as information for evaluating the degree of eccentricity from the center of rotation (axial center of the shaft 110a) of the stage 100 (holder) of the wafer 10. For example, when all of the absolute values at the rotational angle positions θn are smaller than a reference value a:

$$|A_{\theta n} - A_{\theta n+180°}| < a$$

the wafer 10 can be judged to be appropriately set on the stage 100 without eccentricity with respect to the center of rotation of the stage 100.

Further, the absolute value of the difference between the diameter $D_{\theta n}$ at each rotational angle position θn and the diameter $D_{\theta n+90°}$ at the rotational angle position $\theta_{n+90°}$ rotated 90° from the rotational angle position θn $$|D_{\theta n} - D_{\theta n+90°}|$$

can be generated as information for evaluating the degree of circularity of the wafer 10. For example, when all of the absolute values at the rotational angle positions θn are smaller than a reference value d:

$$|D_{\theta n} - D_{\theta n+90°}| < d$$

the wafer 10 can be judged to be have a regular shape (perfect circle).

Further, the absolute value of the difference between the film edge position $C_{\theta n}$ at each rotational angle position θn and the film edge position $C_{\theta n+180}$ at the rotational angle position $\theta_{n+90°}$ rotated 180° from the rotational angle position θn $$|C_{\theta n} - C_{\theta n+180°}|$$

can be generated as information for evaluating the degree of eccentricity of the insulating film 11 to the wafer 10. For example, when all of the absolute values at the rotational angle positions θn are smaller than a reference value c1, $$|C_{\theta n} - C_{\theta n+180°}| < c1$$

the insulating film 11 can be judged to be appropriately formed on the surface of the wafer 10 without eccentricity from the (center of rotation of the) stage 10.

Further, the absolute value of the difference between the radii $Cr_{\theta i}$ and $Cr_{\theta j}$ of the insulating film 11 defined as shown in FIG. 6 based on the film edge position $C_{\theta n}$ at each rotational angle position θn and the film edge positions $C_{\theta n+90°}$, $C_{\theta n+180°}$, and $C_{\theta n+90°+180°}$ at the rotational angle positions $\theta_{n+90°}$, $\theta_{n+180°}$, and $\theta_{n+90°+180°}$ rotated by 90°, 180°, and 270° from the rotational angle position θn:

$$|Cr_{\theta i} - Cr_{\theta j}|$$

$$Cr_{\theta i} = (((C_{\theta n} + C_{\theta n+180°})/2)^2 + ((C_{\theta n+90°} - C_{\theta n+90°+180°})/2)^2)^{1/2}$$

$$Cr_{\theta j} = (((C_{\theta n+90°} + C_{\theta n+90°+180°})/2)^2 + ((C_{\theta n+180°} - C_{\theta n})/2)^2)^{1/2}$$

can be generated as information for evaluating the degree of circularity of the insulating film 11. For example, when all of the absolute values of the differences between the radii $Cr_{\theta i}$ and $Cr_{\theta j}$ of the insulating film 11 obtained based on the film edge positions $C_{\theta n}$ at the rotational angle positions θn etc. are smaller than a reference value c2, $$|Cr_{\theta i} - Cr_{\theta j}| < c2$$

the insulating film 11 can be judged to have a regular shape (perfect circle).

Further, the wafers 10 can be classified based on the absolute value of the difference between the diameters $D_{\theta n}$ and $D_{\theta n+90°}$:

$$|D_{\theta n} - D_{\theta n+90°}|$$

the absolute value between the film edge positions $C_{\theta n}$ and $C_{\theta n+180°}$:

$$|C_{\theta n} - C_{\theta n+180°}|$$

and the absolute value between the radii $Cr_{\theta i}$ and $Cr_{\theta j}$ of the insulating film 11:

$$|Cr_{\theta i} - Cr_{\theta j}|.$$

This classification information can be used as the inspection information (evaluation information).

Specifically, the Classification No. 1 shown in FIG. 7(a) expresses a wafer 10 meeting the conditions:

$$|D_{\theta n} - D_{\theta n+90°}| < d$$

$$|C_{\theta n} - C_{\theta n+180°}| < c1$$

$$|Cr_{\theta i} - Cr_{\theta j}| < c2$$

In this case, as schematically shown in FIG. 9(a), the shape of the outer edge of the wafer 10, the shape of the edge of the insulating film 11, and the position of formation of the insulating film 11 can all be evaluated as normal. Note that FIG. 9(a) only shows this schematically. Of course, the conditions of FIG. 7(a) are not all as shown in FIG. 9(a), but if the wafer shape, state of eccentricity of the insulating film, and shape of the insulating film are displayed on the display unit 220 schematically like in FIG. 9(a) as the evaluation results of the wafer 10, the operator can immediately sense trends of the three by viewing this. This is the same for FIG. 9(b) and beyond.

Classification No. 2 shown in FIG. 7(b) expresses a wafer 10 meeting the conditions:

$$|D_{\theta n} - D_{\theta n+90°}| > d$$

$$|C_{\theta n} - C_{\theta n+180°}| < c1$$

$$|Cr_{\theta i} - Cr_{\theta j}| < c2$$

In this case, as schematically shown in FIG. 9(b), the shape of the edge of the insulating film 11 and the position of formation of the insulating film 11 can be evaluated as normal, but the shape of the outer edge of the wafer 10 can be evaluated as not normal.

Classification No. 3 shown in FIG. 7(c) expresses a wafer 10 meeting the conditions:

$$|D_{\theta n} - D_{\theta n+90°}| > d$$

$$|C_{\theta n} - C_{\theta n+180°}| < c1$$

$$|Cr_{\theta i} - Cr_{\theta j}| > c2$$

In this case, as schematically shown in FIG. 9(c), the position of formation of the insulating film 11 can be evaluated as normal, but the shape of the outer edge of the wafer 10 and the shape of the edge of the insulating film 11 can be evaluated as not normal.

Classification No. 4 shown in FIG. 7(d) expresses a wafer 10 meeting the conditions:

$$|D_{\theta n} - D_{\theta n+90°}| < d$$

$$|C_{\theta n} - C_{\theta n+180°}| < c1$$

$$|Cr_{\theta i} - Cr_{\theta j}| > c2$$

In this case, as schematically shown in FIG. 9(d), the shape of the outer edge of the wafer 10 and the position of formation of the insulating film 11 can be evaluated as normal, but the shape of the edge of the insulating film 11 can be evaluated as not normal.

Classification No. 5 shown in FIG. 8(a) expresses a wafer 10 meeting the conditions:

$$|D_{\theta n} - D_{\theta n+90°}| < d$$

$$|C_{\theta n} - C_{\theta n+180°}| > c1$$

$$|Cr_{\theta i} - Cr_{\theta j}| < c2$$

In this case, as schematically shown in FIG. 9(e), the shape of the outer edge of the wafer 10 and the shape of the edge of the insulating film 11 can be evaluated as normal, but the position of formation of the insulating film 11 can be evaluated as not normal.

Classification No. 6 shown in FIG. 8(b) expresses a wafer 10 meeting the conditions:

$$|D_{\theta n} - D_{\theta n+90°}| > d$$

$$|C_{\theta n} - C_{\theta n+180°}| > c1$$

$$|Cr_{\theta i} - Cr_{\theta j}| < c2$$

In this case, as schematically shown in FIG. 9(f), the shape of the edge of the insulating film 11 can be evaluated as normal, but the shape of the outer edge of the wafer 10 and the position of formation of the insulating film 11 can be evaluated as not normal.

Classification No. 7 shown in FIG. 8(c) expresses a wafer 10 meeting the conditions:

$$|D_{\theta n} - D_{\theta n+90°}| > d$$

$$|C_{\theta n} - C_{\theta n+180°}| > c1$$

$$|Cr_{\theta i} - Cr_{\theta j}| > c2$$

In this case, as schematically shown in FIG. 9(g), the shape of the outer edge of the wafer 10, the shape of the edge of the insulating film 11, and the position of formation of the insulating film 11 can all be evaluated as not normal.

Classification No. 8 shown in FIG. 8(d) expresses a wafer 10 meeting the conditions:

$$|D_{\theta n} - D_{\theta n+90°}| < d$$

$$|C_{\theta n} - C_{\theta n+180°}| > c1$$

$$|Cr_{\theta i} - Cr_{\theta j}| > c2$$

In this case, as schematically shown in FIG. 9(h), the shape of the outer edge of the wafer 10 can be evaluated as normal, but the shape of the edge of the insulating film 11 and the position of formation of the insulating film 11 can be evaluated as not normal.

Returning to FIG. 4, the processing unit 200, after generating inspection information as explained above, performs output processing for displaying predetermined information on the display unit 220 (S6). In this output processing, inspection information such as explained above can be displayed as it is. For example, at each of the plurality of rotational angle positions, all or several of the absolute value of the difference between the wafer edge positions $A_{\theta n}$ and $A_{\theta n+180°}$:

$$|A_{\theta n} - A_{\theta n+180°}|$$

the absolute value of the difference between the diameters $D_{\theta n}$ and $D_{\theta n+90°}$ of the wafer 10:

$$|D_{\theta n} - D_{\theta n+90°}|$$

the absolute value of the difference between the film edge positions $C_{\theta n}$ and $C_{\theta n+180°}$:

$$|C_{\theta n} - C_{\theta n+180°}|$$

and the absolute value of the difference between the radii $Cr_{\theta i}$ and $Cr_{\theta j}$ of the insulating film 11:

$$|Cr_{\theta i} - Cr_{\theta j}|$$

can be displayed on the display unit 220, for example, the values for the rotational angle positions θn can be displayed in a tabular format. By using the information displayed at the display unit 220 in this way, the operator can evaluate the degree of eccentricity and degree of circularity of the wafer 10 being inspected and the degree of eccentricity and degree of circularity of the insulating film 11 more specifically and with a better precision. Based on these evaluations, the suitability of the film forming process of the insulating film 11 and the suitability of the substrate (for example, silicon substrate) forming process of the wafer 10 can be evaluated in more detail.

Further, the processing unit 200 can display at least one of the classification information (No. 1 to No. 8 shown in FIG. 7 and FIG. 8) and the corresponding schematic figures (FIGS. 9(a) to (h)) as evaluation results of the wafer 10 on the display unit 220. In this case, the wafer 10 being inspected can be evaluated macroscopically together with the insulating film 11.

Further, the processing unit 200 generates profile information showing the relationship between each rotational angle position θn and the above-mentioned wafer edge position $A_{\theta n}$, edge-to-edge distance $B_{\theta n}$, and film edge position $C_{\theta n}$ as evaluation information (inspection information) of said wafer 10 and can display the profile information on the display unit 220. In this case, for example, as shown in FIG. 10, the profile Q1 ($A_{\theta n}$) of the wafer edge position $A_{\theta n}$, the profile Q2 ($C_{\theta n}$) of the film edge position $C_{\theta n}$, and the profile Q3 ($B_{\theta n}$) of the edge-to-edge distance $B_{\theta n}$ for one rotation (0° to 360°) of the wafer 10 are shown on the display unit 220. Note that, in FIG. 10, for the wafer edge position $A_{\theta n}$ and film edge position $C_{\theta n}$, the right side scale (147.00 mm to 151.50 mm) is applied, while for the edge-to-edge distance $B_{\theta n}$, the left side scale (0.00 mat to 4.50 mm) is applied. Using such profile information, the shape of the outer edge of the wafer 10, the shape of the edge of the insulating film 11, and the distance between the outer edge of the wafer 10 and the edge of the insulating film (corresponding to the exposed width in the prior art) can be directly grasped.

Note that the outer edge line L1 of wafer 10 based on the wafer edge position $A_{\theta n}$ of each rotational angle position θn and the edge line L2 of the insulating film 11 based on the film edge position $C_{\theta n}$ at each rotational angle position θn can be generated as inspection information of the wafer 10. In this case, as shown in FIG. 11, the outer edge line L1 of the wafer 10 and the edge line L2 of the insulating film 11 are displayed on the display unit 220. In this way, using the outer edge line L1 of the wafer 10 and the edge line L2 of the insulating film 11 displayed on the display unit 220, the shape of the wafer 10, the shape of the insulating film 11, and the position of formation of the insulating film 11 can be accurately evaluated.

Further, the scale resolution for the edge line of the insulating film 11 is set higher than the scale resolution for the outer edge line of the wafer 10 and can be displayed on the display unit 220. That is, only the vicinity of the edge part of the insulating film 11 is displayed enlarging the scale in the diametrical direction of the wafer. In this case, as shown in FIG. 12, the fluctuation of the edge line L20 of the insulating film 11 is emphasized in comparison to the outer edge line L1 of the wafer 10, and the shape and position etc. of the insulating film 11 can be evaluated with better precision and intuitively and clearly by the evaluator.

Note that the inspection information of the wafer 10 is not limited to that explained above. It is not particularly limited so long as information for the wafer 10 obtained based on the wafer edge position $A_{\theta n}$ and edge-to-edge distance $B_{\theta n}$ of each rotational angle position θn.

In the above-mentioned inspecting device, the image obtained by capture by the second camera unit 130b is used only for measuring the wafer edge position $A_{\theta n}$ of each rotational angle position θn (diameter $D_{\theta n}$), however, this image can also be used as inspection results for the back surface side of the wafer 10. For example, in the process of forming the insulating film 11 of the wafer 10, there are cases where the insulating film ends up being wrapped around to the opposite surface from the outer edge of the wafer 10. Defects due to this kind of wraparound of the insulating film can be detected from the images obtained by capture of the second camera unit 130b.

The above-mentioned inspecting device was designed for inspection of a semiconductor wafer 10 on the surface of which a single insulating film 11 is formed, but, as shown in FIG. 13, it can also be designed for inspection of a semiconductor wafer 10 on the surface of which a plurality of, for example, three, insulating films 11a, 11b, and 11c are formed. In the example shown in FIG. 13, the semiconductor wafer 10 is successively formed on its surface with three insulating film 11a, 11b, and 11c so that the higher the layer is, the smaller the diameter.

In the case of this example, the processing unit 200 receives as input the imaging signal from the first camera unit 130a capturing an image of the outer edge and its neighboring region from the surface side of the wafer 10 on which the three insulating films 11a, 11b, and 11c are formed and acquires the corresponding capturing image (image data) (see S1 in FIG. 4). Further, the processing unit 200 measures the edge-to-edge distances $Ba_{\theta n}$, $Bb_{\theta n}$, and $Bc_{\theta n}$ between the outer edge of the wafer 10 and the edges of the insulating films 11a, 11b, and 11c at each rotational angle position θn on the image shown by the image data based on the imaging signal (see S3 in FIG. 4).

The edge-to-edge distances $Ba_{\theta n}$, $Bb_{\theta n}$, and $Bc_{\theta n}$ of the insulating films 11a, 11b, and 11c obtained this way are used, in the same way as in the above-mentioned example, for calculating the film edge positions $Ca_{\theta n}$, $Cb_{\theta n}$, and $Cc_{\theta n}$ for the insulating films 11a, 11b, and 11c (see S4 in FIG. 9). Further, inspection information (evaluation information) regarding each insulating film, for example, information evaluating the degree of eccentricity of the insulating films 11a, 11b, and 11c $|C_{\theta n} - C_{\theta n+180°}|$, information evaluating the degree of circularity of the insulating films 11a, 11b, and 11c $|Cr_{\theta i} - Cr_{\theta j}|$ (see S5 in FIG. 4), and classification information regarding the insulating films 11a, 11b, and 11c (see FIG. 7, FIG. 8, and FIG. 9) can be obtained. Further, inspection information able to express abnormal locations such as overhang in which the film of the upper layer intrudes into the region of the film of the lower layer and largely covers it or undertake in which the film of the upper layer is peeled off or rolled up and the film of the lower layer can be seen can be obtained from the edge-to-edge distances $Ba_{\theta n}$, $Bb_{\theta n}$, and $Bc_{\theta n}$ and edge positions $Ca_{\theta n}$, $Cb_{\theta n}$, and $Cc_{\theta n}$ for the insulating films 11a, 11b, and 11c.

Based on the different types of inspection information for the different insulating films 11a, 11b, and 11c, it is possible to evaluate the quality of the semiconductor wafer 10 and possible to evaluate in more detail the suitability of the film forming process of the insulating films 11a, 11b, and 11c.

The above-mentioned inspecting device was configured so that the first camera unit 130a captured images from the front surface side of the wafer 10 on which the insulating film 11 is formed and the second camera unit 130b captured images from the back surface side of the wafer 10 on which the insulating film 11 is not formed, however, as shown in FIG. 14, it may also be configured so that both the first camera unit 130a and the second camera unit 130b capture images from the front surface side of the wafer 10 on which the insulating film 11 is formed (second example of configuration of the mechanical system). In this case, when two wafer edge positions $A_{\theta n}$ are obtained for each rotational angle position θn based on the images corresponding to the imaging signals from the two first camera unit 130a and second camera unit 130b obtained during one rotation of the wafer 10, their mean value can be made the true wafer edge position $A_{\theta n}$. Further, when two edge-to-edge distances $B_{\theta n}$ are obtained for each rotational angle position θn based on these images, their mean value can be made the true edge-to-edge distance $B_{\theta n}$. Accordingly, inspection with a good precision can be realized. On the other hand, just by rotating the wafer 10 by half, the wafer edge position $A_{\theta n}$ and edge-to-edge distance $B_{\theta n}$ for the full circumference of the wafer 10 can also be obtained. In this case, it is possible to perform a more efficient inspection of the wafer 10.

Further, as shown in FIG. 15, it is possible to provide an edge sensor 132 in place of the second camera unit 130b (third example of configuration of the mechanical system). This edge sensor 132 is arranged on a straight line perpendicular to the center of rotation of the stage 100. A detection signal showing the radial direction position of the outer edge of the wafer 10 set on the stage 100 is output. In this case, the processing unit 200 can determine the true wafer edge position $A_{\theta n}$ from the wafer edge position $A_{\theta n}$ at each rotational angle position θn measured from the image obtained by capture of the first camera unit 130a and the wafer edge position $A_{\theta n}$ at each rotational position θn detected from the detection signal from the edge sensor 132.

Further, the above-mentioned inspecting device was designed to continuously make the wafer 10 rotate and, during that period, inspect and evaluate the wafer 10 based on the images obtained by capture by the first camera unit 130a and the second camera unit 130b at each predetermined rotational angle interval, however, it is also possible to make the stage 100, that is, the wafer 10, rotate intermittently at each predetermined rotational angle.

Further, two camera units 130a and 130b were arranged facing each other separated by 180 degrees in terms of the rotational angle of the stage 100, however, for example, they may also be arranged separated by 90 degrees. The number may also be one or three units. When a plurality of units, it is preferable that they be equally arranged by rotational angles. Further, the device may also be configured arranging the wafer 10 fixed and making the camera units 130a and 130b move rotating along the outer circumference of the wafer 10.

Further, the mechanical system of the inspecting device can be configured as shown in FIG. 16 and FIG. 17 (fourth example of configuration). In this example, two specialized edge sensors 120a and 120b are provided for measuring the diameter of the semiconductor wafer 10, while a single camera unit 130 is provided for capturing an image of the outer edge and its neighboring region of the semiconductor wafer 10.

Specifically, a pair of edge sensors 120a and 120b are provided at predetermined positions in the vicinity of the outer edge of the stage 100. These edge sensors 120a and 120b are arranged on a straight line perpendicular to the center of rotation of the stage 100. Further, the edge sensors 120a and 120b outputs detection signals expressing the radial direction position of the outer edge of the wafer 10 set on the stage 100. Further, a single camera 130 capturing an image of outer edge and its neighboring region of the wafer 10 set on the stage 100 is arranged above the stage 100. The camera 130 includes a CCD line sensor 131 and is set so that the line-shaped image capturing region of the CCD line sensor 131 crosses the outer edge of the wafer 10 on the stage 100 and the edge of the insulating film 11 and is toward the center of rotation of the stage 100. The edge sensors 120a and 120b are arranged at locations offset by exactly ±90 converted to rotational angle of the stage 100 with respect to the direction of arrangement of the CCD line sensor 131.

The processing system of the evaluation system having a mechanical system with such a structure is configured as shown in FIG. 18. In this processing system, the processing unit 200 processes the imaging signals from the camera unit 130 and the detection signals from the two edge sensors 120a and 120b in place of the imaging signals from the first camera units 130a and 130b of the above example (see FIG. 3) and calculates inspection information (evaluation information) the same as the aforementioned.

Specifically, the processing unit 200 performs processing as follows.

Before a wafer 10 is actually evaluated, in the same way as the above example, first, said inspecting device is initialized. In this initialization, for example a dummy wafer confirmed to be a perfect circle and to be accurate in size (for example, diameter 300 mm) is set on the stage 100 using an alignment mechanism (not shown) so that its center accurately matches the center of rotation of said stage 100. Further, the edge sensors 120a and 120b are adjusted in position and the parameters are initialized at the processing unit 200 so that the processing unit 200 accurately recognizes the detection signals from the edge sensor 120a and 120b in the state with the stage 100 rotating as the radial direction positions from the center (shaft) corresponding to the radius (for example, 150 mm) of the dummy wafer.

When the initialization ends, a predetermined operation is performed by the operation unit 210, then, in place of the dummy wafer, the wafer 10 to be evaluated is set on said stage 100 by the alignment mechanism (not shown) so that its center matches the center of rotation of the stage 100 as much as possible, the processing unit 200 performs processing in accordance with the routine shown in FIG. 19.

In FIG. 9, the processing unit 200 receives as input the detection signals from the edge sensors 120a and 120b at each predetermined rotational angle interval while the wafer 10 rotates once at a constant speed and stores these detection signal values as the radial direction positions $A_{\theta n}$ of the outer edge of the wafer 10 shown in FIG. 5 (below referred to as the "wafer edge position") linked with each rotational angle position θn (S11: wafer outer edge position detection step). Here, the rotational angle position θn, in the same way as the above example, means the rotational angle from the notch 10a.

In this regard, when two wafer edge positions $A_{\theta n}$ are obtained for each rotational angle position θn while the wafer 10 is rotating once based on the detection signals from the two edge sensors 120a and 120b, their mean value can be stored linked with the rotational angle position θn as the true wafer edge position $A_{\theta n}$. Further, the wafer edge positions $A_{\theta n}$ corresponding to the rotational angle positions θn of half of the circumference of the wafer 10 can be obtained from the detection signals of one edge sensor 120a, while the wafer edge positions $A_{\theta n}$ corresponding to the rotational angle positions θn of the remaining half of the circumference of the wafer 10 can be obtained from the detection signals of the other edge sensor 120b.

The processing unit 200 receives as input the imaging signal from the camera 130 capturing an image of the outer edge and its neighboring region of the wafer 10 at each predetermined rotational angle interval and stores that imaging signal corresponding to each rotational angle position θn as image data (S12: image capturing step). Further, the processing unit 200 measures the edge-to-edge distance $B_{\theta n}$ between the outer edge of the wafer 10 and the edge of the insulating film 11 at each rotational angle position θn on the image expressed by the image data (S3: edge-to-edge distance measuring step). Specifically, for example, the number of pixels between the outer edge of the wafer 10 and the edge of the insulating film on the image loaded in the memory is measured, and that number of pixels is converted to distance (edge-to-edge distance).

After this, in the same way as the above-mentioned examples, the wafer diameter $D_{\theta_n}$ and the film edge position $C_{\theta_n}$ of the insulating film 11 at each rotational angle position θn are calculated based on the wafer edge position $A_{\theta_n}$ and edge-to-edge distance $B_{\theta_n}$ at each rotational angle position θn (S4). Further, in the same way as explained above, each type of inspection information (evaluation information) is generated (S5). Further, the generated inspection information is displayed, under the control of the processing unit 200, in the same way as in the above example, on the display unit 220 (S6: output processing).

Note that, in each of the above-mentioned examples, an example using the inspecting device for evaluation of the formation of the insulating film at the wafer was explained, however, for example, it is also possible to feed back the inspection results, without accompanying evaluation, to an insulating film or other film-forming device for use for correcting various data at the time of film formation.

Further, in each of the above-mentioned examples, a wafer of a structure on the surface of which an insulating film is formed was explained, however, it may also be a wafer of a structure on the surface of which a conductive film is formed. As a film, a metal film, organic film, compound film, etc. are also conceivable.

Further, as a disc wafer, a semiconductor wafer was explained as an example, however, the invention is not limited to this. It may also be applied to an inspecting device of a disc wafer on the surface of which a processing region is formed, for example, a disc wafer on which a recording layer is formed.

INDUSTRIAL APPLICABILITY

As explained above, the inspecting device and inspecting method of the disc wafer according to the present invention has the effect of enabling higher precision inspection of the processing region formed on the surface of semiconductor wafer or other disc wafer and is useful as an inspecting device and inspecting method for inspection of a disc wafer on the surface of which an insulating film or conductive film or other processing region is formed.

The invention claimed is:

1. An inspecting device of a disc wafer having a processing region formed on its surface, said inspecting device of a disc wafer characterized by having a holder rotatable about a predetermined shaft and holding the disc wafer, a rotation drive part making the holder rotate about the shaft, an image capturing means for capturing an image of the outer edge and its neighboring region of the disc wafer rotated by the rotation of the holder, a wafer outer edge position measuring means for measuring a radial direction position of the outer edge of said disc wafer at each of a plurality of rotational angle positions of the disc wafer rotated by rotation of the holder, an edge-to-edge distance measuring means for measuring an edge-to-edge distance between an outer edge of the disc wafer and an edge of the processing region at each of the plurality of rotational angle positions based on the images captured by the image capturing means, and an inspection information generating means for generating predetermined inspection information based on the radial direction position of the outer edge at each of the plurality of rotational angle positions of the disc wafer obtained by the wafer outer edge position measuring means and the edge-to-edge distance at each of the plurality of rotational angle positions obtained by the edge-to-edge distance measuring means.

2. An inspecting device of a disc wafer as set forth in claim 1 characterized in that the inspection information generating means has a processing region edge position calculating means for calculating radial direction positions of the edge at the plurality of rotational angle positions of the processing region based on the radial direction position of the outer edge at each of the plurality of rotational angle positions of the disc wafer and the edge-to-edge distance at the corresponding rotational angle position and generates inspection information based on the radial direction position of the edge at each of the plurality of rotational angle positions of the processing region.

3. An inspecting device of a disc wafer as set forth in claim 2 characterized in that the inspection information includes information showing inspection results relating to a degree of eccentricity of the processing region to the disc wafer.

4. An inspecting device of a disc wafer as set forth in claim 2 characterized in that the inspection information includes information showing inspection results relating to a degree of circularity of the processing region.

5. An inspecting device of a disc wafer as set forth in claim 1 characterized in that the inspection information generating means comprises a diameter calculating means for calculating a diameter at each of the plurality of rotational angle positions of said disc wafer based on a radial direction position of the outer edge at each of the plurality of rotational angle positions of the disc wafer and generates inspection information based on the diameter at each of the plurality of rotational angle positions of the disc wafer.

6. An inspecting device of a disc wafer as set forth in claim 5 characterized in that the inspection information includes information showing inspection results relating to a degree of eccentricity of the disc wafer to the shaft of the holder.

7. An inspecting device of a disc wafer as set forth in claim 5 characterized in that the inspection information includes information showing inspection results relating to a degree of circularity of the disc wafer.

8. An inspecting device of a disc wafer as set forth in claim 1 characterized in that the inspection information generating means has a processing region edge position calculating means for calculating radial direction positions of the edge at the plurality of rotational angle positions of the processing region based on the radial direction position of the outer edge at each of the plurality of rotational angle positions of the disc wafer and the edge-to-edge distance at the corresponding rotational angle position and a diameter calculating means for calculating a diameter at each of a plurality of rotational angle position of the disc wafer based on the radial direction position of the outer edge at each of the plurality of rotational angle positions of the disc wafer and generates inspection information based on the radial direction position of the edge at each of the plurality of rotational angle positions of the processing region and the diameter at each of the plurality of rotational angle positions of the disc wafer.

9. An inspecting device of a disc wafer as set forth in claim 8 characterized in that the inspection information includes classification information relating to the disc wafer and processing region generated based on the radial direction position of the edge at each of the plurality of rotational angle positions of the processing region and the diameter at each of the plurality of rotational angle positions of the disc wafer.

10. An inspecting device of a disc wafer as set forth in claim 1 characterized in that the wafer outer edge position measuring means measures the radial direction position of the outer edge of said disc wafer at each of the plurality of the rotational angle positions of the disc wafer based on the images captured by the image capturing means.

11. An inspecting device of a disc wafer as set forth in claim 10 characterized in that the image capturing means has a plurality of camera units set so as to be arranged around the disc wafer held by the holder and capturing images of the outer edge and its neighboring region of the disc wafer.

12. An inspecting device of a disc wafer as set forth in claim 11 characterized in that the plurality of camera units have a first camera unit capturing an image of the outer edge and its neighboring region of the disc wafer held by the holder from one surface side and a second camera unit capturing an image of the outer edge and its neighboring region of the disc wafer from the other surface side.

13. An inspecting device of a disc wafer as set forth in claim 12 characterized in that the first camera unit and the second camera unit are arranged offset from each other by a rotational angle of 180 degrees of the disc wafer.

14. An inspecting device of a disc wafer as set forth in claim 12 characterized in that the wafer outer edge position measuring means measures the radial direction position of the outer edge of the disc wafer at each of the plurality of rotational angle positions based on both an image captured by the first camera unit and an image captured by the second camera unit.

15. An inspecting device as set forth in claim 12 characterized in that the edge-to-edge distance measuring means measures the edge-to-edge distance based on the image obtained by the one of the camera units, among the first camera unit and second camera unit, capturing an image from the surface side where the process region is formed.

16. An inspecting method of a disc wafer having a processing region formed on its surface, said inspecting method of a disc wafer characterized by having an image capturing step of capturing an image of an outer edge and its neighboring region of a disc wafer held by a holder rotating about a predetermined shaft and rotating together with said holder, a wafer outer edge position measuring step of measuring a radial direction position of the outer edge of said disc wafer at each of a plurality of rotational angle positions of the disc wafer rotating by the rotation of the holder, an edge-to-edge distance measuring step of measuring an edge-to-edge distance between the outer edge of the disc wafer and the edge of the processing region at each of the plurality of rotational angle positions based on the images captured at the image capturing step, and an inspection information generating step of generating predetermined inspection information based on the radial direction position of the outer edge at each of the plurality of rotational angle positions of the disc wafer obtained by the wafer outer edge position measuring step and the edge-to-edge distance at each of the plurality of rotational angle positions obtained at the edge-to-edge distance measuring step.

17. An inspecting method of a disc wafer as set forth in claim 16, characterized in that the inspection information generating step includes a processing region edge position calculating step of calculating the radial direction position of the edge at each of the plurality of rotational angle positions of the processing region based on the radial direction position of the outer edge at each of the plurality of rotational angle positions of the disc wafer and the edge-to-edge distance at the corresponding rotational angle position and a diameter calculating step of calculating the diameter at each of the plurality of rotational angle positions of the disc wafer based on the radial direction position of the outer edge at each of the plurality of rotational angle positions of the disc wafer and generates inspection information based on the radial direction position of the edge at each of the plurality of rotational angle positions of the processing region and the diameter at each of the plurality of rotational angle positions of the disc wafer.

18. An inspecting method of a disc wafer as set forth in claim 16, characterized in that the wafer outer edge position measuring step measures the radial direction position of the outer edge of said disc wafer at each of the plurality of rotational angle positions of the disc wafer based on the images captured by the image capturing step.

* * * * *